(12) United States Patent
Madrazo et al.

(10) Patent No.: US 8,673,313 B2
(45) Date of Patent: *Mar. 18, 2014

(54) CELL PENETRATING PEPTIDES AND ITS USE FUSED TO BIOMOLECULES WITH THERAPEUTIC ACTION

(75) Inventors: Isis del Carmen Torrens Madrazo, Ciudad de la Habana (CU); Maribel Guerra Vallespi, Ciudad de la Habana (CU); Milaid Granadillo Rodriguez, Ciudad de la Habana (CU); Osvaldo Reyes Acosta, Ciudad de la Habana (CU); Boris Ernesto Acevedo Castro, Ciudad de la Habana (CU)

(73) Assignee: Centro de Ingenieria Genetica y Biotecnologia, Ciudad de la Habana (CU)

( * ) Notice: Subject to any disclaimer, the term of this patent is extended or adjusted under 35 U.S.C. 154(b) by 410 days.

This patent is subject to a terminal disclaimer.

(21) Appl. No.: 12/671,335

(22) PCT Filed: Jul. 31, 2008

(86) PCT No.: PCT/CU2008/000006
§ 371 (c)(1),
(2), (4) Date: Feb. 17, 2012

(87) PCT Pub. No.: WO2009/021468
PCT Pub. Date: Feb. 19, 2009

(65) Prior Publication Data
US 2012/0135021 A1    May 31, 2012

(30) Foreign Application Priority Data
Jul. 31, 2007   (CU) .................................. 2007-0180

(51) Int. Cl.
*A61K 39/12* (2006.01)
*A61K 39/02* (2006.01)

(52) U.S. Cl.
USPC ................... 424/186.1; 424/196.1; 424/278.1

(58) Field of Classification Search
None
See application file for complete search history.

(56) References Cited

U.S. PATENT DOCUMENTS 8,283,324 B2 * 10/2012 Vallespi et al. .............. 514/21.4

OTHER PUBLICATIONS

Roth RI et al. Limulus antilipopolysaccharide factor prevents mortality late in the course of endotoxemia. J Infect Dis. Feb. 1998;177(2):388-94.*
Muta T et al. Primary structure of anti-lipopolysaccharide factor from American horseshoe crab, Limulus polyphemus. J Biochem. Jun. 1987;101(6):1321-30.*
Hanly WC et al. Review of Polyclonal Antibody Production Procedures in Mammals and Poultry. ILAR J. 1995;37(3):93-118.*

* cited by examiner

*Primary Examiner* — Stacy B. Chen
*Assistant Examiner* — Nick Zou
(74) *Attorney, Agent, or Firm* — Hoffmann & Baron, LLP

(57) ABSTRACT

The present invention relates to use of a new cell penetrating peptides (CPP) and in particular to the region 32.-51 of protein *Limulus antilipopolisacárido* (LALF) and its analogous. This invention refers to compositions containing these peptides associated to biomolecules with therapeutics properties. This invention consist of compositions comprise the covalent fusion of biomolecules, between this human papillomavirus antigens (HPV) to these CPP for induce a potent immune cellular responses against HPV and HPV protein antigen-exhibiting cells including HPV-associated tumors. The referred compositions are applicable in the pharmaceutical industry as vaccine for therapeutic use in human.

12 Claims, 9 Drawing Sheets

CELL PENETRATING PEPTIDES AND ITS USE FUSED TO BIOMOLECULES WITH THERAPEUTIC ACTION

CLAIM OF PRIORITY

This application is the U.S. National Phase of, and Applicants claim priority from, International Application Number PCT/CU2008/000006 filed 31 Jul. 2008 and Cuban Patent Application No. 2007-0180 filed 31 Jul. 2007, which are incorporated herein by reference.

INCORPORATION OF SEQUENCE LISTING

Incorporated herein by reference in its entirety is the Sequence Listing for the above-identified Application. The Sequence Listing is disclosed on a computer-readable ASCII text file titled "SeqList976_71PCTUS.txt", modified on Feb. 16, 2012. The sequence.txt file is 9.06 KB.

TECHNICAL FIELD

The present invention is directed to the fields of immunology, cell biology, and cancer. Specifically, the methods and compositions of the present invention involve the fusion of biomolecules of different origin to cell penetrating peptides (CPP) for induction a potent therapeutic action.

STATE OF THE PREVIOUS TECHNIQUE

During the last decade, several proteins, such as HIV-1 Tat, *Drosophila* Antennapedia homeoprotein, and HSV-1 VP22 have been shown to traverse the cell membrane by a process called protein transduction and to reach the nucleus while retaining their biological activity (Prochiantz, A. (2000) Messenger proteins: homeoproteins, TAT and others. *Curr. Opin. Cell Biol.* 12: 400-406). Indeed, it was discovered that short peptides derived from protein-transduction domains (cell-penetrating peptides or CPP) can be internalized in most cell types. These CPP have been successfully used for the intracellular delivery of biomolecules (Schwarze, S. R. et al. (2000) Protein transduction: unrestricted delivery into all cells?. *Trends Cell Biol.* 10:290-295). A wide range of biomolecules such as antigenic peptides, peptide nucleic acids, oligonucleotides, full-length proteins, nanoparticles and liposomes have been delivered this way. Most drugs are poorly taken up in cells, and this is considered a major limitation in their development as therapeutic agents. The fusion of therapeutic agents to CPP could thus become a strategy of choice to improve their pharmacological properties.

Several CPP have been identified, from proteins, including the Tat protein of human immunodeficiency virus (Frankel, A. D., and Pabo, C. O. (1988) Cellular uptake of the Tat protein from human immunodeficiency virus. *Cell* 55:1189-1193), the VP22 protein of herpes simplex virus (Elliott, G., and O'Hare, P. (1997) Intercellular trafficking and protein delivery by a herpesvirus structural protein. *Cell* 88:223-233), and the fibroblast growth factor (Rojas M, et al. (1998) Genetic engineering of protein with cell. membrane permeability. *Nat. Biotechnol.* 16:370-375). The Tat peptide has been used to transduce proteins into cells both in vitro and in vivo (Lindgren, M et al. (2000) Cell-penetrating peptides. *Trends Pharmacol. Sci.* 21:99-103). The use of these CPP in delivering tumor antigens into cells may prolongs the efficient presentation of peptide to T cells, leading to the generation of potent immune response against cancer.

About one percent of women worldwide are affected with cervical cancer. According to the World Health Organization, cancers of the cervix have been plagued on five hundred thousand or more women around the world every year and particularly in the less developed countries the cancer of cervix is the main cause of women deaths.

HPVs are now recognized as the major cause of cervical cancer. Studies also suggest that HPVs may play a role in cancers of the anus, vulva, vagina, and some cancers of the oropharynx (the middle part of the throat that includes the soft palate, the base of the tongue, and the tonsils) (Division of STD Prevention. *Prevention of genital HPV infection and sequelae: Report of an external consultants' meeting.* Atlanta, Ga.: Centers for Disease Control and Prevention, 1999).

HPV are a group of more than 100 viruses. Over 30 types are usually transmitted sexually. Some types of HPV are referred to as "low-risk" viruses because they rarely develop into cancer. HPV types that are more likely to lead to the development of cancer are referred to as "high-risk." Both high-risk and low-risk types of HPV can cause the growth of abnormal cells, but generally only the high-risk types of HPV may lead to cancer. Sexually transmitted, high-risk HPVs include types 16, 18, 31, 33, 35, 39, 45, 51, 52, 56, 58, 59, 68, 69, and possibly a few others. These high-risk types of HPV cause growths that are usually flat and nearly invisible.

Genital warts (technically known as condylomata acuminatum) are most commonly associated with two low-risk HPV types, HPV-6 and HPV-11. Papillomaviruses are small (50-60 nm) no enveloped DNA viruses, having a double-stranded, circular DNA genome of 7800 to 7900 base pairs. The genome contains three major regions, one coding for late genes, one coding for early genes and a non-coding region (Park T. W. et al. (1995) Molecular biology of cervical cancer and its precursors. *Cancer* 76:1902-1913). The late gene region has two separate open reading frames encoding viral capsid proteins L1 (major) and L2 (minor). The early gene region includes six open reading frames, designated E1, E2, E4, E5, E6 and E7. Proteins E6 and E7 are oncoproteins critical for viral replication as well as for host cell immortalization and transformation.

Methods commonly used to treat lesions include cryosurgery (freezing that destroys tissue), LEEP (loop electrosurgical excision procedure, the removal of tissue using a hot wire loop), and conventional surgery. Similar treatments may be used for external genital warts. In addition, some drugs may be used to treat external genital warts (Centers for Disease Control and Prevention. Sexually transmitted diseases treatment guidelines 2002. Centers for Disease Control and Prevention. *Morbidity and Mortality Weekly Report* 2002; 51 (RR-6):1-78). Recently, the U.S. Food and Drug Administration (FDA) approved a prophylactic vaccine for preventing infection with types 16 and 18, two "high-risk" HPVs that cause most (70 percent) cervical cancers, and types 6 and 11, which cause most (90 percent) genital warts (Koutsky L A, Ault K A, Wheeler C M, et al. A controlled trial of a human papillomavirus type 16 vaccine. *New England Journal of Medicine* 2002; 347(21):1645-1651).

Several therapeutic vaccines have been proposed for the treatment of lesions associated to the HPV. For example the U.S. Pat. No. 6,306,397 (CSL Limited) describes variants of E6/E7 of HPV to generate an immune cellular response; WO 93/20844 (Cancer Research Campaign Technology) talks about to the use of a vaccine against HPV based on the E7 protein. The patents WO 92/10513 (The University of Queensland); U.S. Pat. No. 5,547,846 (Behringwerke Aktiengeellschaft) and U.S. Pat. No. 6,013,258 (Zycos Inc.)

describe peptides that constitute the antigenic component of the vaccine against HPV. The U.S. Pat. No. 6,524,825 (Stressgen Biotechnologies) proposes the use of the fusion of E7 with the heat shock protein (Hsp) as vaccine for the therapy of lesions produced by HPV.

The results of clinical trials with these vaccines, as the results of others therapeutic vaccines using different tumor antigens has met with only limited success (Dallal R. M. and Lotze M. T. (2000) The dendritic cell and human cancer vaccines *Curr Opin Immunol* 12:583-588), because tends to elicit weak self-reactive T cell responses. Thus, a major challenge in cancer vaccines is how to break self-tolerance and generate strong, long-lasting antitumor immunity through manipulation of both the antigen and delivery system.

The present invention in contrast to the state of the previous technique, proposes the use of a new family of CPP and the compositions comprise HPV antigens are genetically fused to this new family of CPP, which enhancement the cellular immune response against antigens of the HPV and against HPV protein antigen-exhibiting cells including HPV-associated tumors.

EXPLANATION OF THE INVENTION

This invention solves the problem mentioned above, providing a new family of CPP which can be used as a platform for fusion biomolecules and achieve effective internalization of drugs into cells. The new family of CPP consists of the peptide corresponding to the region 32-51 of LALF protein (SEQ ID N0. 1) and analogous peptide from this one with point substitutions of amino acid in different positions for the alanine amino acid: L-2 (SEQ ID N0. 2, substitution in the position 2), L-8 (SEQ ID N0. 3, substitution in the position 8), L-12 (SEQ ID N0. 4, substitution in the position 12) y L-20 (SEQ ID N0. 5, substitution in the position 20).

In a particular embodiment, the present invention provides a pharmaceutical composition containing HPV antigens genetically fused to the family of CPP previously mentioned that potency the immune response against HPV antigens, where antigen protein of HPV are covalently fused to the CPP family. This genetic fusion guarantees the delivery of HPV antigen to cells, ensuring the processing of the cargo protein and the presentation to T cells of antigenic epitopes for a long time, resulting in a cellular immune response and antitumor powerful.

The immune response can be a cellular response, in particular a cell-mediated, cytolytic response to an HPV protein antigen. The compositions can be used therapeutically. In the therapeutic application, induction of an immune response in a subject refers to the generation of responses that exceed, either in magnitude or in quality, responses previously elicited by contact with HPV protein antigens exhibited either by the virus or by infected or transformed cells of the subject.

In particular embodiments, the pharmaceuticals compositions are used to generate immune responses to tumor cells expressing and exhibiting an HPV protein antigen. In these embodiments, preferred HPV protein antigens targeted by the compositions are the E6 and E7 early viral proteins that are known to be consistently expressed in HPV-associated tumors.

In one embodiment, the pharmaceuticals compositions comprise an HPV E6 or E7 protein antigen fused to LALF CPP at the nucleotide level permitting expression and purification of a protein containing both E6/E7 antigens and LALF CPP sequences. The fusion protein can be mixed with adjuvants.

The compositions can also be used therapeutically in a subject previously infected with an HPV to prevent further viral proliferation or to eliminate cells of the subject that proliferate as a consequence of HPV infection, including tumors expressing and exhibiting an HPV antigen or presenting a portion of the antigen.

When reference is made herein to an HPV protein antigen as a target of an immune response induced by a pharmaceutical composition of the present invention, the HPV protein antigen is understood to include an entire HPV protein or a polypeptide portion of the HPV protein exhibited on the surface of HPV or an infected cell of a subject as well as peptide displayed by an infected cell as a result of processing and presentation of the HPV protein, for example, through the typical MHC class I or II pathways.

The genomic sequences of many different types of HPV were cloned and were characterized by DNA sequence analysis. Bacterial vectors containing complete or partial HPV genomes are available from various sources including, for example, the American Tissue Culture Collection (ATCC). Additional types of HPV useful for the practice of the present invention can be isolated and typed by the methods previously established for this purpose, which methods are well known in the art.

Of particular importance in the application of the present invention to the therapeutic treatment of HPV-associated cancers is the observation that HPV E6 and E7 proteins are consistently expressed in cervical cancers ((Zur Hausen H. (1987) Papillomaviruses in human cancer. *Appl Pathol* 5:19-24; Pater M. M., Pater A. (1985) Human papillomavirus types 16 and 18 sequences in carcinoma cell lines of the cervix. *Virology* 145:313-318).

Finally, animals' model studies demonstrate that immunization with an E7 protein protects mice against a challenge with lung cells transformed with an activated c-Ha-ras gene and HPV E6/E7 genes (Lin K. Y. et al. (1996) Treatment of established tumors with a novel vaccine that enhances major histocompatibility class II presentation of tumor antigen. *Cancer Res.* 56:21-26). From the points of view that these proteins are typically expressed in cancers arising as a consequence of HPV infection, that the same proteins are also the oncogenes which most likely played a major role in the development and maintenance of the cancers, and that an immune response can be directed against these proteins, E6 and E7 are preferred targets for immune intervention or prophylaxis, and, hence, are preferred HPV protein antigens of pharmaceutical compositions of the present invention to be used to prevent or treat HPV-associated cancer.

The pharmaceutical compositions described herein can be used to enhance an immune response, in particularly a cell-mediated cytolytic response against an HPV, or HPV-infected or transformed cell expressing an HPV antigen. These compositions can be administered to a subject in a variety of ways. The routes of administration include intradermal, transdermal, intramuscular, intraperitoneal, intravenous, subcutaneous, oral, epidural and intranasal routes. Any other convenient route of administration can be used, for example, infusion or bolus injection, or absorption through epithelial or mucocutaneous linings. In addition, the compositions described herein can contain and be administered with adjuvant. Furthermore, the compositions can be used ex vivo as a means of stimulating white blood cells obtained from a subject to elicit, expand and propagate HPV protein antigen-specific immune cells in vitro that are subsequently reintroduced into the subject.

The effective amount is the amount such that when administered, it induces an immune response against the HPV protein antigen which it encodes. In addition, the amount of pharmaceutical compositions administered to the subject can vary depending on a variety of factors, including the HPV protein antigen, or antigens, the size, age, body weight, general health, sex and diet of the subject as well as on its general immunological responsiveness.

EXAMPLES

Example 1

Internalization of CPP LALF or their Analogues to Cells with Different Histological Origins Different cellular lines were used in this realization (Table 1). Cells grown on sterile glass cover slips of 22 mm overnight at 37° C. and 5% of CO2 with RPMI 1640, 10% inactivated calf fetal serum and 2 mM de glutamine. Then, 25 or 50 µM de CPP LALF or their biotinylated analogues L-2 y L-20 added and incubated at 37° C. and 4° C. in different times (10 min, 20 min, 30 min, 1 h y 2 h). Wash briefly with PBS and fix cells by 4% paraformaldehide per 20 min at room temperature. Wash in three changes of PBS. The permeabilization of the cells was with 0.5% Tritón X-100 for 15 min a room temperature. Wash in three changes of PBS. The cells were incubating for 1 hour in 1% blocking SFB in PBS at room temperature. Wash in three changes of PBS. Incubate with 1:50000 in PBS streptavidin-fluorescein for 45 minutes in a dark chamber. Wash extensively with PBS. Mount cover slip with aqueous mounting medium. Examine using a fluorescence microscope with appropriate filters.

TABLE 1

Internalization of CPP LALF or their analogues to cells with different histological origins

| Cells | Peptide CPP (µM) | Temperature (° C.) | Time |
|---|---|---|---|
| J774 | 25 µM LALF | 37° C., | 10 min, 20 min, |
|  | 50 µM LALF | 4° C. | 30 min, 1 h, 2 h, |
| CasKi | 50 µM LALF | 37° C. | 30 min, 1 h, 2 h |
| HeLa | 50 µM LALF | 37° C. | 30 min, 1 h, 2 h |
| TC-1 | 50 µM LALF | 37° C. | 30 min, 1 h, 2 h |
| Hep2 | 50 µM LALF | 37° C. | 30 min, 1 h, 2 h |
|  | 50 µM L-2 |  |  |
|  | 50 µM L-20 |  |  |

As a negative control were used not related biotinylated and cells without peptide.

Figure 1:
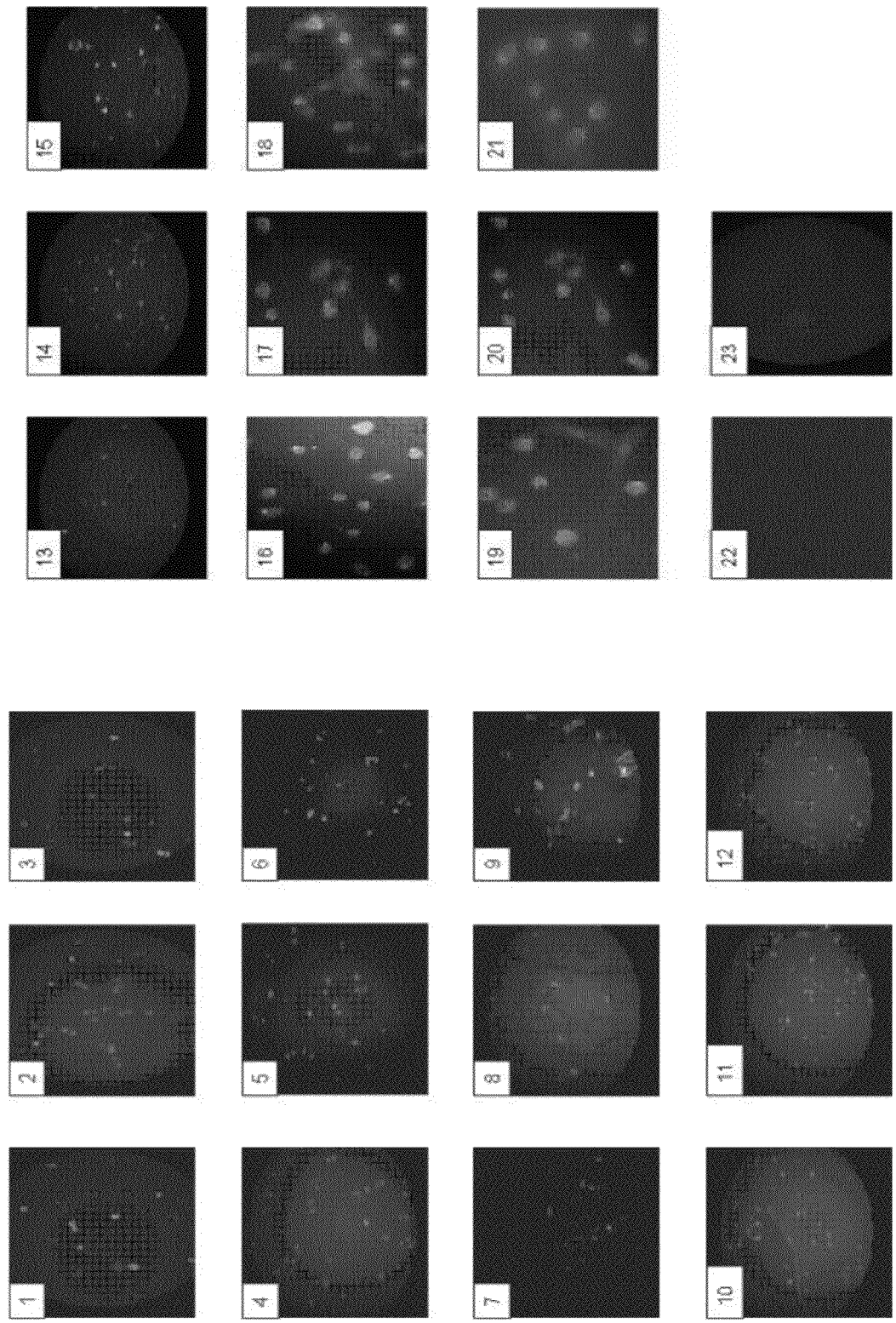
FIG. 1. Fluorescence microscopy image showing the penetration capacity of LALF CPP into cells
1—LALF in J774 at 37° C. for 10 min
2—LALF in J774 at 37° C. for 20 min
3—LALF in J774 at 37° C. for 30 min
4—LALF in J774 at 4° C. for 10 min
5—LALF in J774 at 4° C. for 20 min
6—LALF in J774 at 4° C. for 30 min
7—LALF in CaSki at 37° C. for 30 min
8—LALF in CaSki at 37° C. for 1 h
9—LALF in CaSki at 37° C. for 2 h
10—LALF in HeLa at 37° C. for 30 min
11—LALF in HeLa at 37° C. for 1 h
12—LALF in HeLa at 37° C. for 2 h
13—LALF in TC-1 at 37° C. for 30 min
14—LALF in TC-1 at 37° C. for 1 h
15—LALF in TC-1 at 37° C. for 2 h
16—L-2 in Hep-2 at 37° C. for 30 min
17—L-2 in Hep-2 at 37° C. for 1 h
18—L-2 in Hep-2 at 37° C. for 2 h
19—L-20 in Hep-2 at 37° C. for 30 min
20—L-20 in Hep-2 at 37° C. for 1 h
21—L-20 in Hep-2 at 37° C. for 2 h
22—J774 cells (negative control)
23—No related peptide in J774 at 37° C. for 2 h FIG. 2. Fluorescence microscopy image showing the penetration capacity of L-2 and L-20 into cells
1a and 1b. Not treated cells (negative control)
2a and 2b. Cells treated during 10 min with L-2 peptide
3a and 3b. Cells treated during 10 min with L-20 peptide
4a and 4b. Cells treated during 30 min with L-2 peptide
5a and 5b. Cells treated during 30 min with L-20 peptide
6a and 6b. Cells treated during 1 h with L-2 peptide
7a and 7b. Cells treated during 1 h with L-20 peptide
8a and 8b. Cells treated during 18 h with L-2 peptide
9a and 9b. Cells treated during 18 h with L-20 peptide FIG. 3. Schematic representation of construct pPEPE7M-7

The results showed (FIG. 1) that the CFP LALF and their analogues are internalized in different cell types and short incubation times (30 min). Additionally, CPP LALF was internalized in the cells J774 with only 10 min of the incubation at 4° C., that confirm the characteristics of these peptides as CPP, whose route used for internalization is independent of endocytosis.

These results are similar when using the analogues L-8 and L-12.

Example 2

Internalization of the Analogues L-2 and L-20 to Murine Splenocytes

Figure 2:
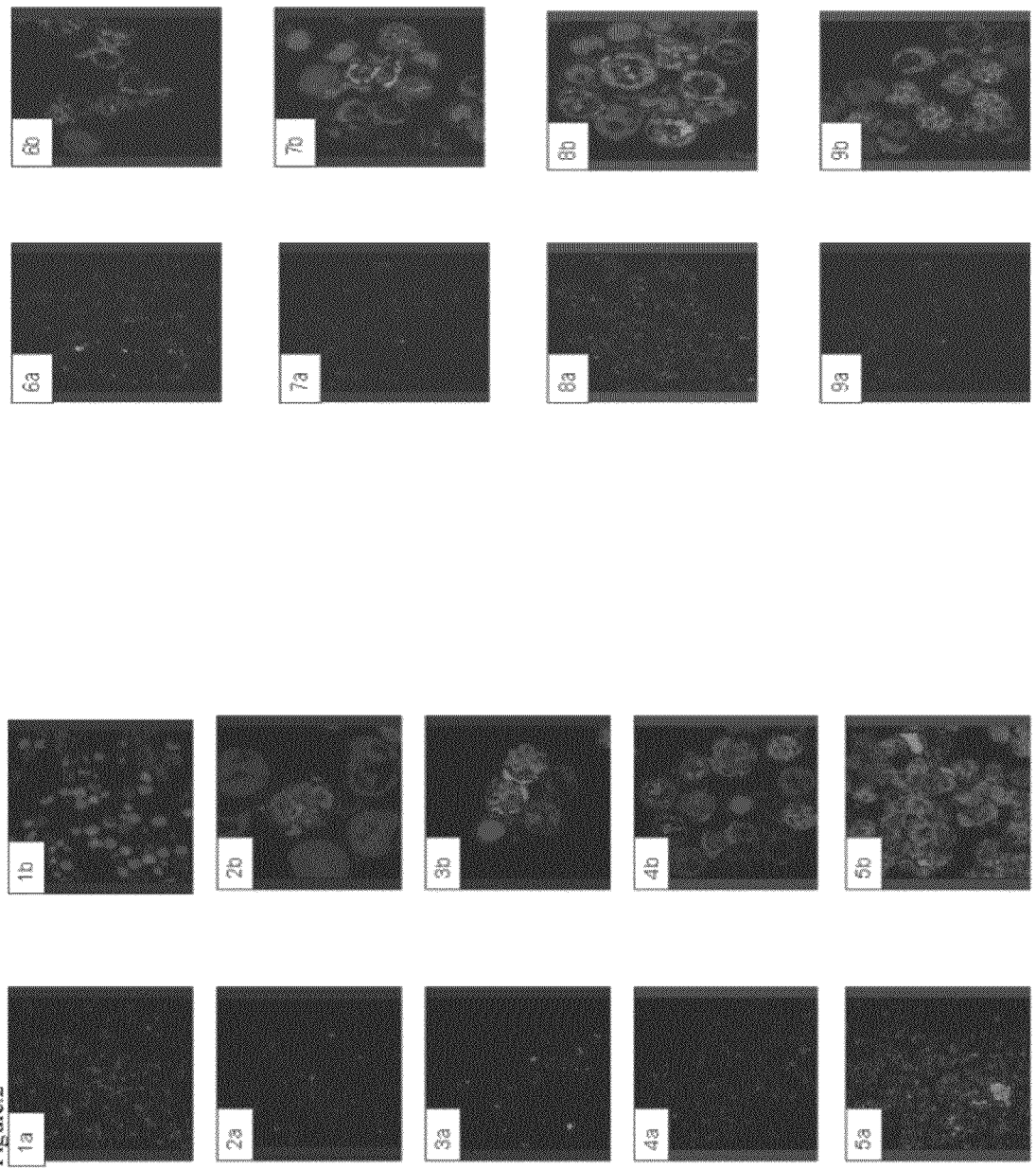

For the splenocytes isolation, the mice C57BL/6 were sacrificed by break-up of the cervical and the splenocytes were removed aseptically. The cellular suspensions of the animals by each group met in pool and they were homogenized smoothly. The splenocytes were washed and the erythrocytes were lysed with a solution of $NH_4Cl$ 0.83%. After washing, the splenocytes are divided en different tubes with $20 \times 10^6$ of cells in 10 mL of fresh medium RPMI 1640 supplemented with 7% de fetal bovine serum. Each preparation was incubated with 0.8 mg of the biotinylated peptides L-2 (278 μM) y L-20 (280 μM) in different times: 10 min, 30 min, 1 h and 18 h. The incubations were at 37° C. and 5% de CO2. The cells on sterile glass cover slips were fixed, permeabilized and treated with propidium Iodide for to stain the nucleus and with streptavidine-fluorescein for detection of peptides inside the cells. The obtained results by confocal microscopy (FIG. 2) showed that the peptides L-2 and L-20 internalized in a short times of incubation (30 min).

These results are similar when using the CPP LALF and analogues L-8 and L-12.

Example 3

Cloning and Expression of Recombinant Fusion Protein CPP LALF or Analogues with E7

The chemical synthesis of the two chains of DNA from CPP LALF was performed in order to obtain the recombinant fusion of CPP LALF to E7 protein. The DNA fragment of CPP LALF (SEQ ID N0. 6) contain in the 5' and 3' ends, the sites open restrictions sites NcoI and HindIII, respectively. The E7 of HPV 16 DNA sequence contains in the 5' and 3' ends, the sites open restrictions sites HindIII and BamHI, respectively. Also contain in the triplet codifying for the first E7 cystein, a substitution of the T per G, in order to eliminate the site of recognition pf E7 to Rb protein (SEQ ID N0. 7). Both synthetic fragments inserted with the uses of T4 ligase en the vector pM238 (Yero D. et al (2006) Bicistronic expression plasmid for the rapid production of recombinant fused proteins in *Escherichia coli*. Biotechnol Appl Biochem. 44:27-34) previously digested with NcoI and BamHI. This vector contains the *E. coli* tryptophan promoter and the termination signal of the bacteriophage T4 (T4 terminator) that allows it to be used for the protein expression in *E. coli*. Also contain at the 3' end a sequence of 6 histidines that allows a purification of protein by affinity metals chromatography.

Figure 3:
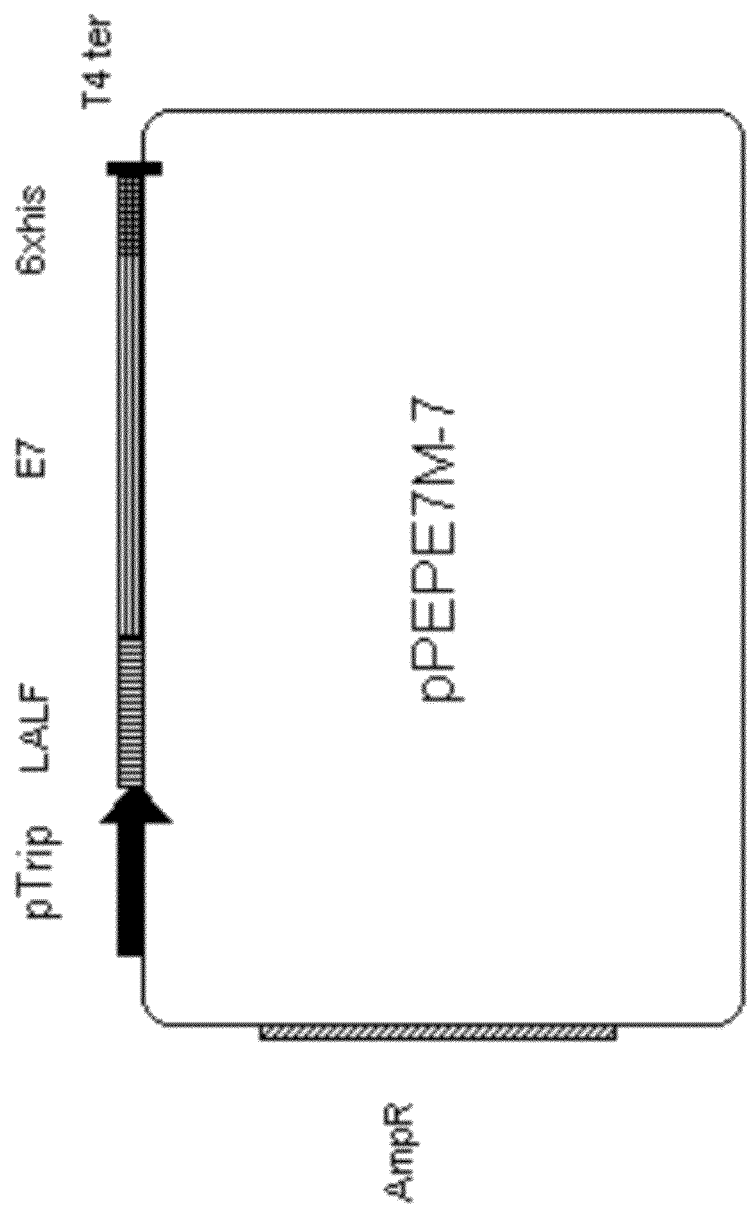

The ligation reaction was transformed into a preparation of competent cells of *E. coli*. The obtained transformed cells were examined by analysis with 5 restriction enzymes. In addition, the positive clones were examined by sequence of double chain, using for it sense primer of 27 bases (SEQ ID N0. 8) that hybrid with the E7, and the correct fusion protein (SEQ ID N0. 9 y 10) and substitution of cysteine per glycine in the union site to Rb protein was corroborated. The clone (FIG. 3) was denominated pPEPE7M-7.

These results are similar when in the site of CPP LALF was used any of their analogues L-8 and L-12.

Example 4

Fermentation and Purification of Recombinant Fusion Protein CPP LALF or Analogues with E7

The pPEPE7M-7 plasmid was transformed into the *E. coli* strain BL-21. The transforming clones were put under processes of fermentation in the minimal medium containing M9 SALT and supplemented with 0.1M $CaCl_2$, 0.1M $MgCl_2$, 1% glucose, 1% casein hydrolizate 0.5% triptone and 100 μg/mL ampicillina during 24 hours at 37° C. with agitation of 250 rpm. After 9 hours of fermentation with approximately 1 optical density at 620 nm, was added 40 μg/mL indolacrilic acids to induce the expression of recombinant protein. This induction was maintained during 15 hours. The sedimentation of the cells was made by a centrifugation to 10.000 rpm by 20 minutes to 4° C.

Five grams of biomass were suspended in 25 mL of a tampon solution of 50 mM $NaH_2PO_4$; 0.3 M NaCl; pH 8, was put under a cellular rupture in ultrasound, (0.5 cycles, 70 of amplitude by 1 minute). The rupture process was made 5 times. The broken cells were homogenized and centrifuged 10.000 rpm by 30 minutes at 4° C. The supernatant of this centrifugation was eliminated, and the insoluble fraction that contains the recombinant protein for its purification was collected.

Three precipitated grams were washed with 30 mL of the buffer solution 50 mM Tris-HCl; 3 mM EDTA; 0.8 M NaCl; 0.01 M $MgCl_2$; 0.1% NP40 and the homogenization was made in a Polytron at a rotation speed of 9.500 per 1 minute. The homogenized was centrifuged to 10.000 rpm per 20 minutes at 4° C. The supernatant was eliminated of the centrifugation and the insoluble fraction was suspended in the 30 mL of the buffer solution 50 mM $NaH_2PO_4$; 0.3 M NaCL; pH 8 and Ia homogenization was performed as described previously. The homogenized was centrifuged to 10.000 rpm per 20 minutes at 4° C. In order to do the extraction of the protein of the insoluble fraction, 1 gram of the protein were suspended in 100 mL of 4 M Urea in buffer 50 mM $NaH_2PO_4$; 0.3 M NaCl, pH 8. The homogenization was made with a Polytron at a speed of rotation of 9.500 per 1 minute. After that the extraction was centrifuged to 10.000 rpm by 20 minutes at 4° C. The soluble fraction was separated from the extraction, which contained the interest protein. This fraction was applied to a column of Ni-NTA (His-Select™ Nickel Affinity Gel, Sigma) equilibrated with 4 M en buffer 50 mM $NaH_2PO_4$; 0.3 M NaCL; pH 8 y 5 mM imidazol. The column was washed with the same equilibration buffer and 40 mM imidazol and the elution of protein was performed with 250 mM imidazol.

The purified protein was dialyzed with buffer Tris 1× pH 8.4 using membrane of 10 μm of diameter. Finally the protein was sterilized by filtration through a filter of 0.22-μm.

These results are similar when in the site of CPP LALF was used any of their analogues L-2, L-8, L-12 y L-20.

Example 5

Demonstration by Fluorescence Microscopy that the CPP LALF or Their Analogues Internalize the Cargo Protein E7 to the Cell Cells J774 grown on sterile glass cover slips of 22 mm overnight at 37° C. and 5% of CO2 with RPMI 1640, 10% inactivated calf fetal serum and 2 mM de glutamine. Then, different glass cover slips incubated with 1.66 μM fusion protein LALF-E7, 1.66 μM of protein E7 and PBS (as negative control) a 37° C. per 30 min, 1 hour and 2 hours. CasKi cells (human cells expressing HPV 16) grown as positive control in the same experimental conditions.

After incubation the cells were washed briefly with PBS and fix cells by 4% paraformaldehyde per 20 min at room temperature. Wash in three changes of PBS. The permeabilization of the cells was with 0.5% Tritón X-100 for 15 min a room temperature. Wash in three changes of PBS. Then, the cells were incubating for 1 hour in 1% blocking SFB in PBS at room temperature. Wash in three changes of PBS. Cells were incubated with goat IgG anti E7/HPV 16 polyclonal antibody (Santa Cruz) diluted in PBS 1:50. Wash extensively with PBS. Incubate with anti-goat-fluorescein IgG polyclonal antibody (Santa Cruz) diluted in PBS 1:50 for 45 minutes in a dark chamber. Wash extensively with PBS. Mount cover slip with aqueous mounting medium. Examine using a fluorescence microscope with appropriate filters.

Figure 4:
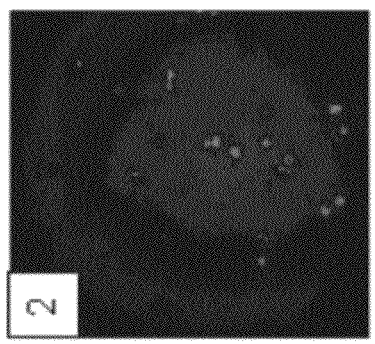
FIG. 4. Fluorescence microscopy image showing the penetration capacity of LALF-E7 into cells
1—LALF-E7 in J774 at 37° C. for 30 min
2—LALF-E7 in J774 at 37° C. for 1 h
3—LALF-E7 in J774 at 37° C. for 2 h
4—E7 in J774 at 37° C. for 2 h
5—PBS in J774 at 37° C. for 2 h
6—CaSki FIG. 5. Western blot showing the internalization of LALF-E7 into the cells
1—J774
2—J774+E7
3—J774+LALF-E7
4—LALF-E7
Figure 4:
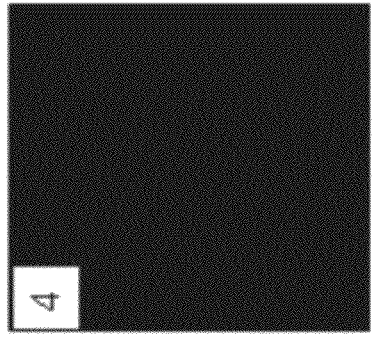
Figure 4:
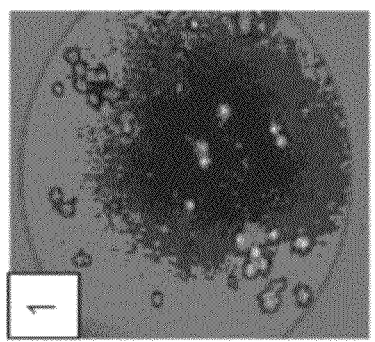
Figure 4:
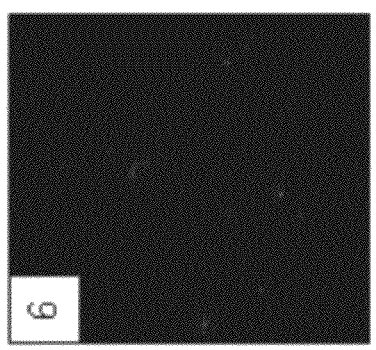
Figure 4:
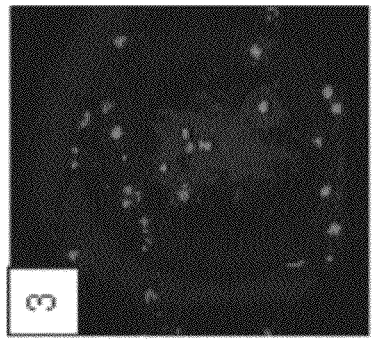
Figure 4:
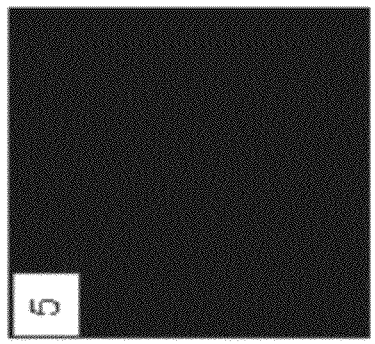

The results showed (FIG. 4) fluorescent cells only in the case when J774 cells incubated with the fusion LALF-E7 and in the CasKi cells. Negative results obtained with the incubation of J774 with E7 and PBS. These results show that the E7 protein achieves its internalization into the cell only in the case when it is fusion to LALF.

These results are similar when in the site of CPP LALF was used any of their analogues L-2, L-8, L-12 y L-20.

Example 6

Figure 5:
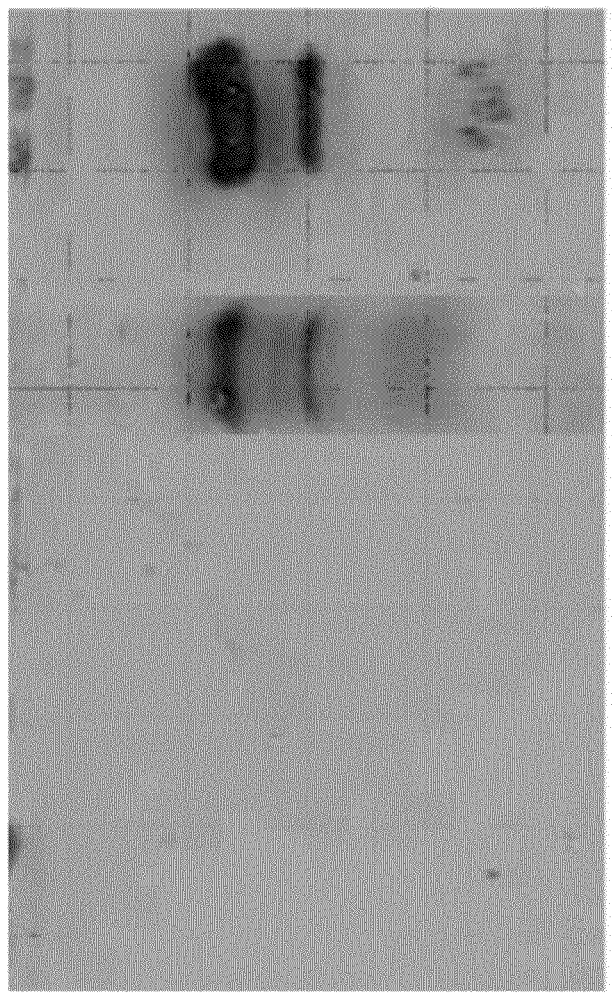

Demonstration by Western Blot that the CPP LALF or Their Analogues Internalize the Cargo Protein to the Cell The cells J774 grown overnight at 37° C. and 5% of CO2 with RPMI 1640, 10% inactivated calf fetal serum and 2 mM de glutamine. After that, the cell were aliquoted in tubes with $5 \times 10^6$ cells each and incubated with 25 µM of fusion protein LALF-E7, 25 µM of protein E7 and PBS during 4 hours at 37° C. The sedimentation of the cells was made by a centrifugation to 1000 rpm by 10 minutes. Wash pellet in three changes of PBS. Cells were ruptured in 100 µL of RIPA buffer (Promega) mixed in vortex per 10 second and 2 min in ice. The sedimentation of the broken cells was made by a centrifugation to 12000 rpm by 15 minutes. Protein concentration was determined to the cell extract and rum 10 µg of total protein in 15% polyacrilamide gel. Subsequently the gel was transferred to a nitrocellulose membrane. The membrane was incubated for 2 hours at room temperature with an IgG goat polyclonal antibody anti-E7 HPV 16 (Santa Cruz) diluted in PBS (1:100). Wash in three changes of PBS. Subsequently, the membrane was incubated for 45 minutes at room temperature and in a dark room with an anti-goat IgG peroxidase conjugate (Sigma) diluted in PBS (1:5000). Wash in three changes of PBS. Finally the ECL system from Amersham Pharmacia Biotech was used. As shown in FIG. 5 were able to extract sufficient quantities of the fusion protein (LALF-E7) inside cells J774 after a short incubation time in vitro cells with the protein, which was recognized by the anti-E7 antibody. But was not detected any recognition in the lane where it was applied extract the cells incubated with the E7 protein and PBS.

These results are similar when in the site of CPP LALF was used any of their analogues L-2, L-8, L-12 y L-20.

Example 7

Demonstration by Fluorescence Microscopy that the CPP LALF or Their Analogues Internalize the Cargo Protein GFP to the Cell The protein produced in *E. coli* from the recombinant fusion LALF-GFP (GFP-English, green fluorescence protein) was used to verify that the CPP LALF or its analogues could internalize the cargo protein. The GFP (GenBank Accession #U55762) was obtained using the polymerase chain reaction from plasmid pEGFP-N1 of Clontech using oligonucleotides with SEQ ID N0. 11 and 12. Both oligonucleotides have restricted sites used for cloning (HindIII-sense and BamHI-antisense).

For the construction of recombinant fragment, synthetic LALF and GFP gene obtained by PCR were inserted with the T4 ligase in the vector pM238, similar as in the example III. The recombinant clone is identified with the SEQ ID N0. 13 and 14.

With the recombinant and purified LALF-GFP protein was performed an similar experiment to the example V, but in this case the cells J774 incubated with LALF-GFP, LALF biotinilade, GFP and PBS.

Figure 6:
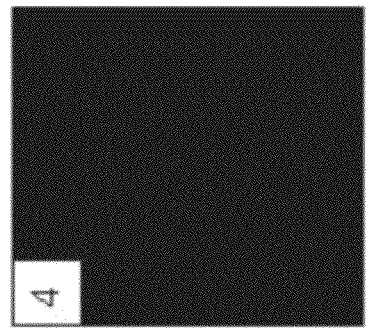
FIG. 6. Fluorescence microscopy image showing the penetration capacity of LALF-GFP into cells
1—LALF-GFP
2—LALF biotin
3—GFP
4—PBS FIG. 7. Graph showing the effect of treatment with LALF-E7 on tumor on established tumor volume of TC-1 cells in mice FIG. 8. Graph showing that the effect of treatment with LALF-E7 on tumor on established tumor volume of TC-1 cells in mice is dependent of covalent fusion of protein.
Figure 6:
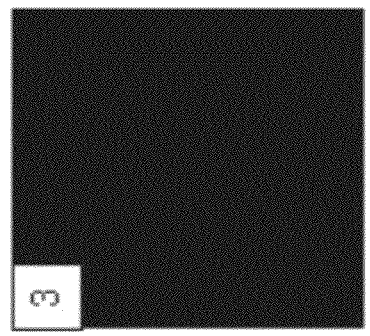
Figure 6:
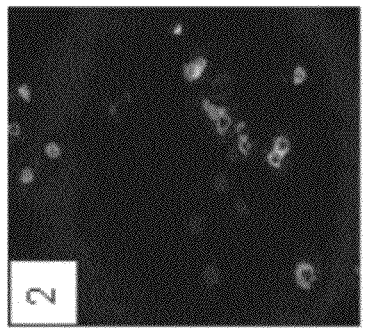
Figure 6:
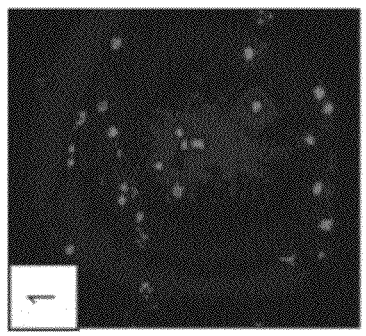

The obtained results (FIG. 6) showed fluorescent cells when J774 cells were incubated with the fusion LALF-GFP, similar to those obtained by the LALF-biotinilado. Not fluorescent cells were observed with the incubation of J774 with GFP and PBS.

These results show that the cargo protein, in this case the GFP achieves its internalization into the cell only when it is fusion to LALF.

These results are similar when instead CPP LALF used any of their analogues L-2, L-8, L-12 and L-20.

Example 8

Treatment of Established Tumors in Mice with Fusion Proteins of CPP LALF or its Analogous with E7 (LALF+E7)

In order to observe the regression of established tumors from the treatment with the recombinant protein fusion LALF-E7, the tumor cell line TC-1, was used. The TC-1 tumor cell line expressing the HPV16 E7 protein was derived from primary lung cells of C57Bl/6 mice by immortalization and transformation with HPV16 E6 and E7 genes and an activated human C-Ha-ras gene as described in Lin et al. (1996)) Treatment of established tumors with a novel vaccine that enhances major histocompatibility class II presentation of tumor antigen. *Cancer Res.* 56:21-26. For tumor inoculation, TC-1 cells, supplied by Dr. T.-C. Wu (The Johns Hopkins Medical Institutions, Baltimore, Md.), were grown to 60-70% confluence in RPMI1640 medium supplemented with 10% fetal calf serum (Hyclone, Logan, Utah), nonessential amino acids, glutamine, pyruvate, gentamycin, beta-mercaptoethanol and 0.4 mg/mL Geneticin at 37° C. Cells were harvested by trypsinization and resuspended in Hank's buffer solution at $2.5 \times 10^5$ cells/mL.

Figure 7:
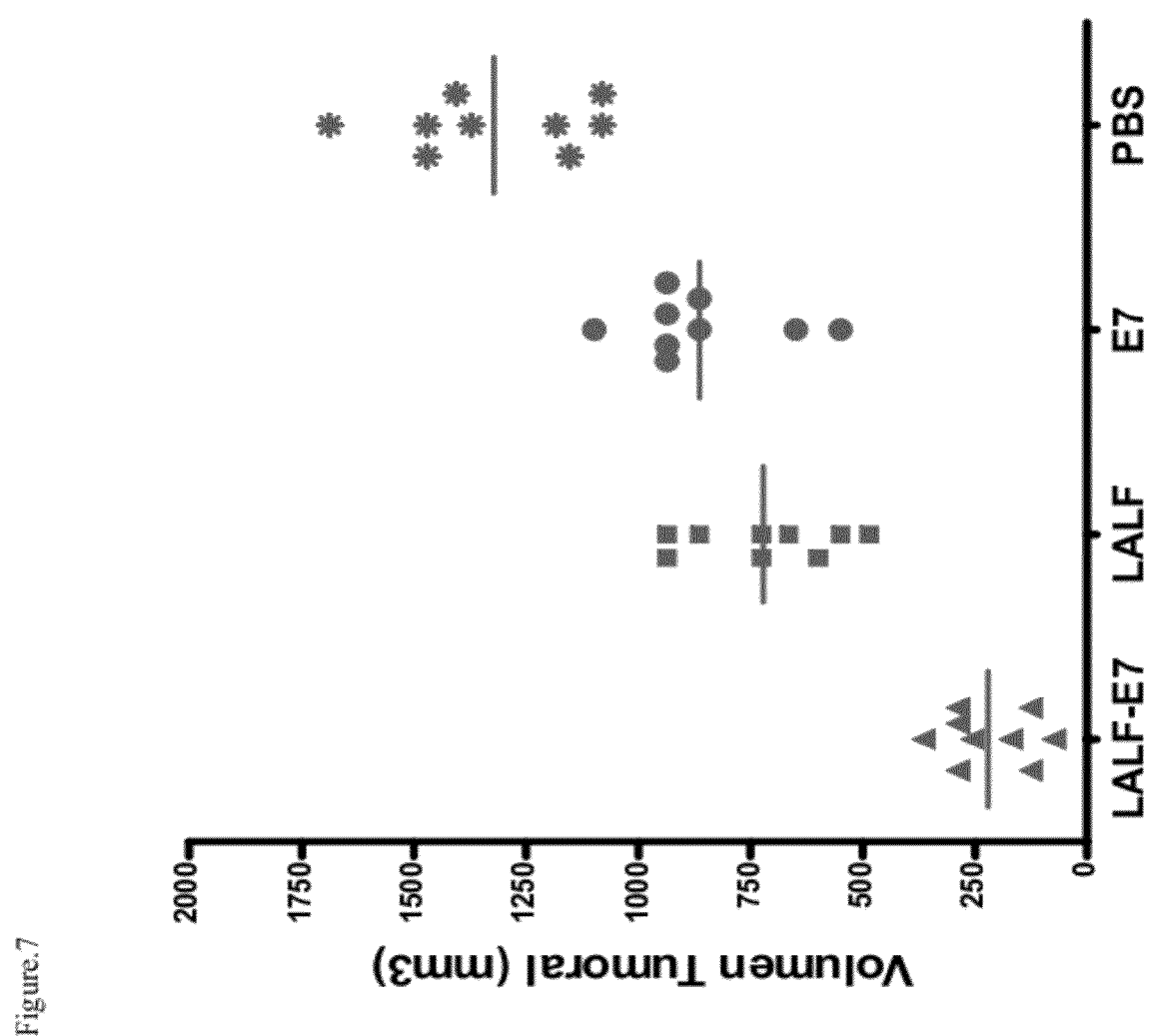

Mice C57BL/6 was inoculated with $2 \times 10^5$ cells by subcutaneous injection in right leg in volumes of 0.2 mL. To the 10 days, when all the animals had developed palpable tumors, the animals were assigned arbitrarily to four groups of treatments. Each group included 10 animals. Two immunizations, every 14 days were made. The group 1 was immunized with the recombinant protein LALF-E7; group 2 with the recombinant protein E7; group 3 with synthetic peptide LALF and group 4 with PBS. The tumor kinetic in the different groups was followed by the tumor volume which was determined using electronic calipers and taking the measures in two orthogonal dimensions. Tumor volumes (mm$^3$) were calculated from these measurements according to (length×width$^2$)/2. The volume average of each group +/− the standard deviation at the 30 days is represented in the FIG. 7.

The results demonstrate that the treatment with LALF-E7 results in a full inhibition of growth of established tumors. These results are statistically significant compared with the results obtained with others treatments as E7, LALF and PBS (p<0.01). Similar results are obtaining with the fusion protein of E7 with analogous of LALF CPP as L2, L-8, L-12 and L-20.

Example 9

Treatment of Established Tumors in Mice with Fusion Proteins of CPP LALF or its Analogous with E7 (LALF-E7) and the Mix of CPP LALF or its Analogous with E7 (LALF+E7)

To study whether the antitumor effect of LALF-E7 was associated with the covalent bond of both molecules, we carried out experiments in which mice were treated for LALF and E7, which were mixed at the time prior to their use at equal molarity that would allow a comparison with mice that received the fusion protein LALF-E7.

In this realization, Mice C57BL/6 was inoculated with $2\times10^5$ cells by subcutaneous injection in right leg in volumes of 0.2 mL. To the 10 days, when all the animals had developed palpable tumors, the animals were assigned arbitrarily to five groups of treatments. Each group included 10 animals.

Figure 8:
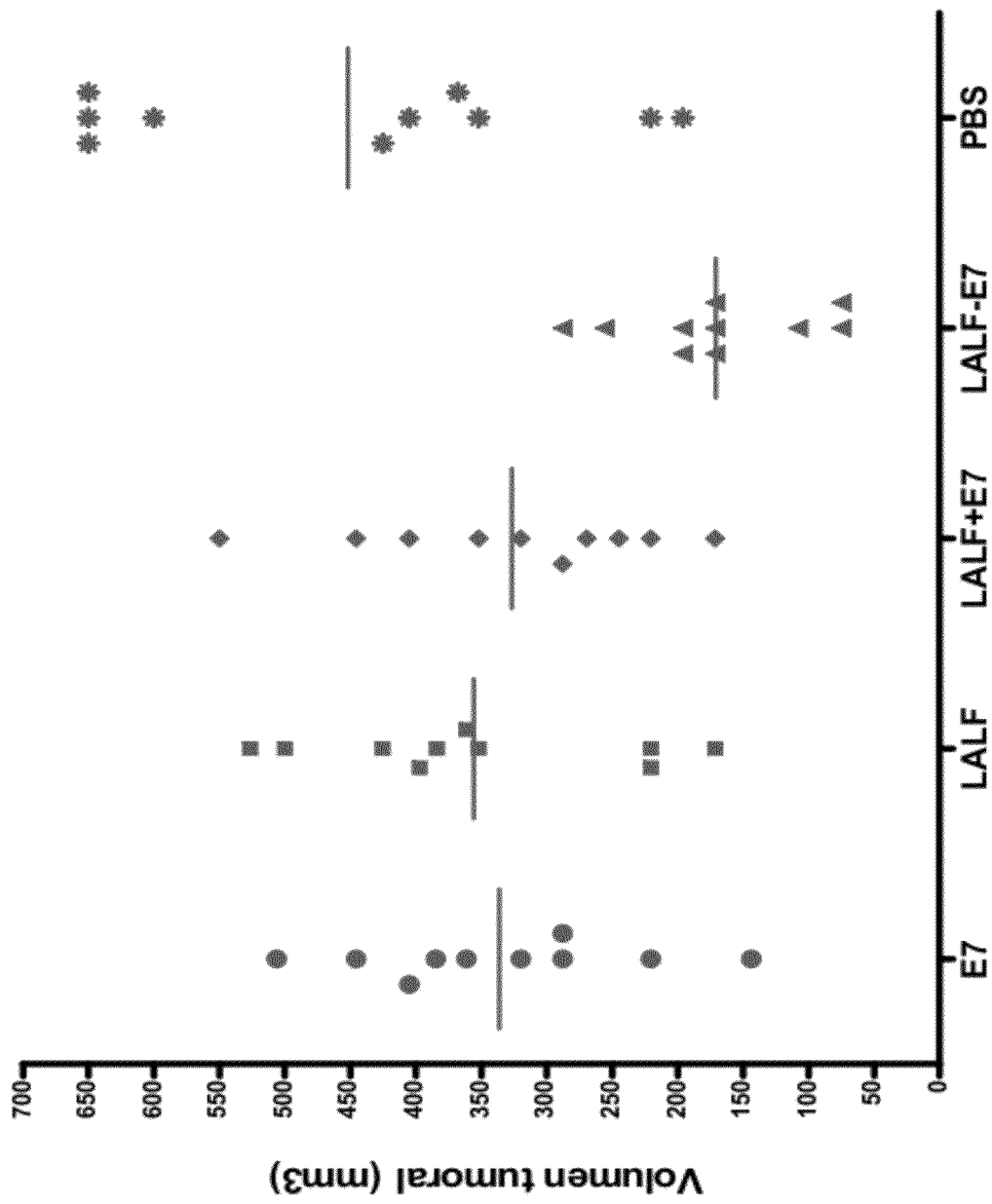

Two immunizations, every 14 days were made. The group 1 was immunized with the recombinant protein LALF-E7; group 2 with the mix LALF+E7: recombinant protein E7; group 3 with synthetic peptide LALF; group 4 with recombinant protein E7 and group 5 with PBS. The tumor kinetic in the different groups was followed as previously described in the example 8. The volume average of each group +/− the standard deviation at the 30 days is represented in the FIG. 8.

The results showed that the effects in reducing the volume of tumors can be seen only with the treatment of mice with the covalent fusion LALF-E7, whose results were statistically significant when compared with the volumes resulting from treatment with the mixture of LALF+E7, LALF, E7 and PBS ($p<0.01$).

These results are similar when instead CPP LALF used any of their analogues L-2, L-8, L-12 and L-20.

Example 10

Comparison of the Ability of Pharmaceuticals Compositions to Induce Cellular Immune Responses In order to evaluate the cellular immune response against the antigen E7 de HPV-16, 4 groups of 3 mice females C57BL/6, from 6 to 8 weeks of born, received 2 doses of immunogens. The group 1 was immunized with the 30 µg of the recombinant protein LALF-E7; group 2 with the 30 µg of the recombinant protein E7; group 3 with 8 µg of synthetic peptide LALF and group 4 with PBS. The immunizations were made of subcutaneous way in the flank of the animal with volumes of 0.2 mL and without adjuvant. Every 14 days were administered two doses. Seven days after the second immunization, the mice were sacrificed by break-up of the cervical and the splenocytes were removed aseptically for their later analysis in a test of ELISPOT anti-gamma interferon (anti-IFN-$\gamma$). The cellular suspensions of the animals by each group met in pool and they were homogenized smoothly. The splenocytes were washed and the erythrocytes were lysed with a solution of $NH_4Cl$ 0.83%. Later they were washed and finally they were suspended in fresh RPMI 1640 medium supplemented with 10% of fetal bovine serum (FBS) and 10 U/mL of human IL-2 (hIL-2). Cells of mouse EL4 ($H-2^b$), which they do not express E7 HPV-16 epitopes were used as target cells, which previously were pulsed to a concentration of 10 µM with peptide $^{49}$RAHYNIVTF$^{57}$ corresponding to CTL epitope of mouse C57BL/6, $H-2^b$ (Feltkamp M. G. et al. (1993) Vaccination with cytotoxic T lymphocyte epitope containing peptide protects against a tumor induced by human papillomavirus type 16-transformed cells. *Eur. J. Immunol.* 23:2242-2249). Later the cells were suspended in supplemented RPMI 1640 with 10% of FBS and hIL-2, and used as antigen presenting cells. The EL4 cells not pulsed were also including for the determination of the background of secretors cells of IFN-$\gamma$.

The test for the determination of the IFN-$\gamma$ secretion was made as described previously (Vazquez-Blomquist D. et al. (2002) Induction of a strong HIV-specific CD8+ T cell response in mice using a fowlpox virus vector expressing an HIV-1 multi-CTL-epitope polypeptide. *Viral Immunol.* 5(2): 337-356). The plates of 96 wells with the bottom covered with paper of nitrocellulose were recovered with 100 µL of 5 µg/mL of the capture Ab and they were incubated over night to 4° C. After three washings with PBS, the plates were blocked with RPMI 1640 supplemented with 10% FBS by one hour at 37° C. The splenocytes ($10^6$, $2\times10^5$ and $4\times10^4$ cells by well) and EL4 cells ($10^5$ by well) were added respectively in a final volume of 0.2 mL and co-incubated in duplicate to 37° C. and 5% of $CO_2$ by 17 hours. After the incubation, a standard ELISPOT was tested (Vazquez-Blomquist D. et al. (2002) Induction of to strong HIV-specific CD8+ T cell response in mice using to fowlpox virus vector expressing an Hiv-1 multi-CTL-epitope polypeptide. *Viral Immunol.* 5(2): 337-356). For the determinations of re-stimulated in vitro lymphocytes, $2.8\times10^7$ of splenocytes cells of each condition was incubated with EL4 cells loaded with the peptide and hIL-2, during 7 days at 37° C., in a humid atmosphere with 5% of $CO_2$. After this time, the surviving cells counted and were used for determinations of ELISPOT under the same conditions.

The results were expressed as a number of spot forming cells (SFC) per $10^6$ splenocytes. The number of SFC was obtained from the count of the points by means of stereoscopy and the frequency is obtained by relate the number of them to the number of cells incubated in each well.

Positive were considered those values that were the double of the negative control (EL4 without peptide) plus 10 SFC.

Figure 9:
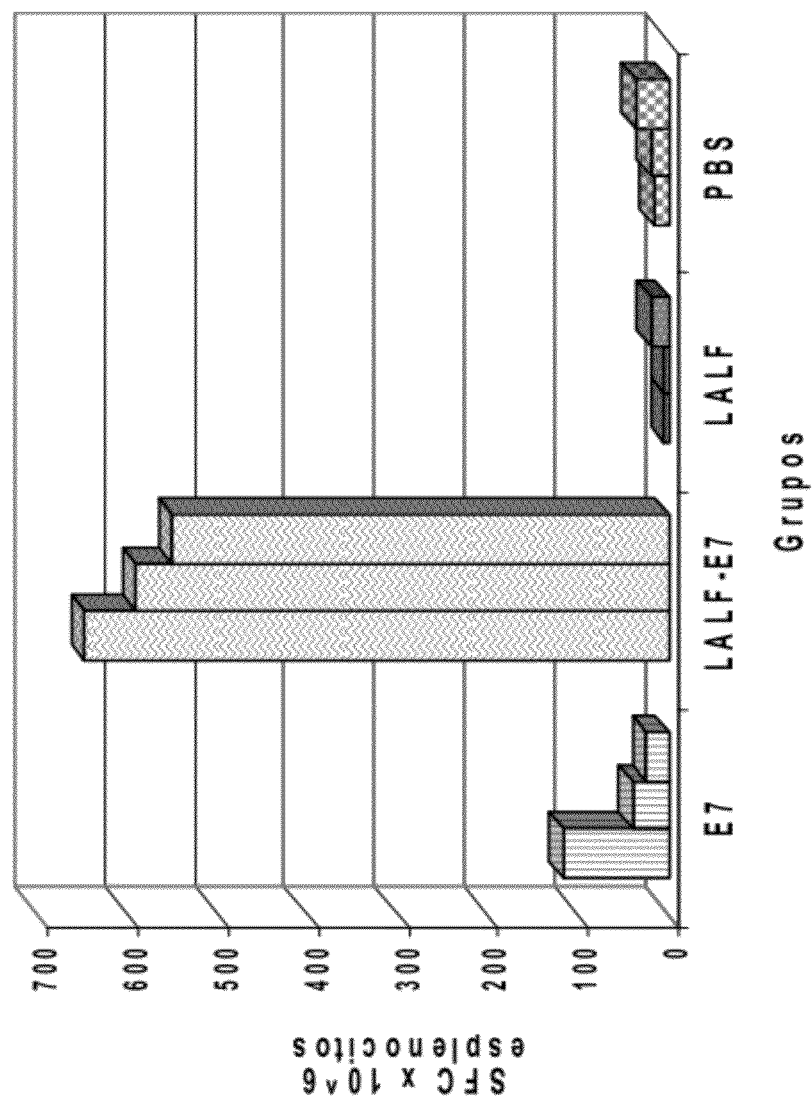
FIG. 9. Graph showing the count of spot formed effectors cells (SFC) per $10^6$ of de splenocytes pool of 3 mice immunized with different preparations.

As shown in FIG. 9, the number of effectors secretors cells of $\gamma$-IFN is that is number SFC was superior up to 8 times approximately in the groups immunized with LALF-E7 respect to the groups immunized with VSSP and PBS.

These results demonstrate the existence of an effective response of T CD8$^+$ lymphocytes in the animals treated with LALF-E7.

These results are similar when instead CPP LALF used any of their analogues L-2, L-8, L-12 and L-20.

The invention claimed is:

1. A composition comprising an isolated biomolecule fused to a cell penetrating peptide selected from the group consisting of SEQ ID NOS: 1 to 5, wherein said biomolecule is a viral, bacterial, or tumor antigen.

2. The biomolecule of claim 1 wherein said viral antigen is a Human Papilloma Virus (HPV) antigen.

3. The biomolecule of claim 2 wherein said HPV antigen is an E6 or E7 protein.

4. A pharmaceutical composition comprising the composition of claim 1.

5. The pharmaceutical composition according to claim 4, wherein the cell penetrating peptide and biomolecule are associated by covalent bond or conjugation.

6. The pharmaceutical composition according to claim 5 wherein said viral antigen is an HPV antigen.

7. The pharmaceutical composition according to claim 6, wherein said HPV antigen is an E6 or E7 protein.

8. The pharmaceutical composition according to claim 4, wherein said composition additionally comprises an adjuvant.

9. The pharmaceutical composition according to claim 8, wherein said adjuvant is a complete adjuvant, an incomplete adjuvant or an adjuvant of polypeptide nature.

10. A pharmaceutical composition that comprises a LALF peptide fused to HPV16 E7 protein identified as SEQ. ID. NO: 10.

11. A method for treatment of tumors expressing an HPV protein antigen, comprising administering to a human an effective amount of the pharmaceutical composition of claim 6, to enhance the cellular immune response against HPV.

12. A fusion protein consisting of SEQ ID NO: 10.

* * * * *

UNITED STATES PATENT AND TRADEMARK OFFICE
CERTIFICATE OF CORRECTION

PATENT NO. : 8,673,313 B2
APPLICATION NO. : 12/671335
DATED : March 18, 2014
INVENTOR(S) : Madrazo et al.

It is certified that error appears in the above-identified patent and that said Letters Patent is hereby corrected as shown below:

IN THE SPECIFICATION:

Column 7, Line 4

Now Reads: "$NH_4$ C10.83%"
Should Read: "$NH_4Cl$ 0.83%"

Signed and Sealed this
Fourth Day of November, 2014

Michelle K. Lee
*Deputy Director of the United States Patent and Trademark Office*

SEQUENCE LISTING

<160> NUMBER OF SEQ ID NOS: 14

<210> SEQ ID NO 1
<211> LENGTH: 20
<212> TYPE: PRT

-continued

```
<213> ORGANISM: Artificial Sequence
<220> FEATURE:
<223> OTHER INFORMATION: Artificial Sequence Description: Synthetic Gen
      CPP LALF

<400> SEQUENCE: 1

His Tyr Arg Ile Lys Pro Thr Phe Arg Arg Leu Lys Trp Lys Tyr Lys
 1               5                  10                  15

Gly Lys Phe Trp
            20

<210> SEQ ID NO 2
<211> LENGTH: 20
<212> TYPE: PRT
<213> ORGANISM: Artificial Sequence
<220> FEATURE:
<223> OTHER INFORMATION: Artificial Sequence Description: Analogue L-2

<400> SEQUENCE: 2

His Ala Arg Ile Lys Pro Thr Phe Arg Arg Leu Lys Trp Lys Tyr Lys
 1               5                  10                  15

Gly Lys Phe Trp
            20

<210> SEQ ID NO 3
<211> LENGTH: 20
<212> TYPE: PRT
<213> ORGANISM: Artificial Sequence
<220> FEATURE:
<223> OTHER INFORMATION: Artificial Sequence Description: Analogue L-8

<400> SEQUENCE: 3

His Tyr Arg Ile Lys Pro Thr Ala Arg Arg Leu Lys Trp Lys Tyr Lys
 1               5                  10                  15

Gly Lys Phe Trp
            20

<210> SEQ ID NO 4
<211> LENGTH: 20
<212> TYPE: PRT
<213> ORGANISM: Artificial Sequence
<220> FEATURE:
<223> OTHER INFORMATION: Artificial Sequence Description: Analogue L-12

<400> SEQUENCE: 4

His Tyr Arg Ile Lys Pro Thr Phe Arg Arg Leu Ala Trp Lys Tyr Lys
 1               5                  10                  15

Gly Lys Phe Trp
            20

<210> SEQ ID NO 5
<211> LENGTH: 20
<212> TYPE: PRT
<213> ORGANISM: Artificial Sequence
<220> FEATURE:
<223> OTHER INFORMATION: Artificial Sequence Description: Analogue L-20

<400> SEQUENCE: 5

His Tyr Arg Ile Lys Pro Thr Phe Arg Arg Leu Lys Trp Lys Tyr Lys
 1               5                  10                  15

Gly Lys Phe Ala
            20

<210> SEQ ID NO 6
<211> LENGTH: 75
```

```
<212> TYPE: DNA
<213> ORGANISM: Artificial Sequence
<220> FEATURE:
<223> OTHER INFORMATION: Artificial Sequence Description: Synthetic Gen
      CPP LALF

<400> SEQUENCE: 6
catggcggaa ttccattatc gtatcaaacc gacctttcgt cgtctgaaat ggaaatataa      60
aggcaaattt tggaa                                                       75

<210> SEQ ID NO 7
<211> LENGTH: 299
<212> TYPE: DNA
<213> ORGANISM: Artificial Sequence
<220> FEATURE:
<223> OTHER INFORMATION: Artificial Sequence Description: Synthetic Gen
      E7 HPV 16

<400> SEQUENCE: 7
agcttcacat ggagatacac ctacattgca tgaatatatg ttagatttgc aaccagagac      60
aactgatctc tacggttatg agcaattaaa tgacagctca gaggaggagg atgaaataga     120
tggtccagct ggacaagcag aaccggacag agcccattac aatattgtaa ccttttgttg     180
caagtgtgac tctacgcttc ggttgtgcgt acaaagcaca cacgtagaca ttcgtacttt     240
ggaagacctg ttaatgggca cactaggaat tgtgtgcccc atctgttctc agaaaccag     299

<210> SEQ ID NO 8
<211> LENGTH: 27
<212> TYPE: DNA
<213> ORGANISM: Artificial Sequence
<220> FEATURE:
<223> OTHER INFORMATION: Artificial Sequence Description: Synthetic
      Oligo for sequencing

<400> SEQUENCE: 8
ttatggtttc tgagaacaga tggggca                                          27

<210> SEQ ID NO 9
<211> LENGTH: 405
<212> TYPE: DNA
<213> ORGANISM: Artificial Sequence
<220> FEATURE:
<223> OTHER INFORMATION: Artificial Sequence Description: Gen fusion CPP
      LALF-E7

<400> SEQUENCE: 9
atggcggaat tccattatcg tatcaaaccg acctttcgtc gtctgaaatg gaaatataaa      60
ggcaaatttt ggaaagcttc acatggagat acacctacat tgcatgaata tatgttagat     120
ttgcaaccag agacaactga tctctacggt tatgagcaat aaatgacag ctcagaggag     180 gaggatgaaa tagatggtcc agctggacaa gcagaaccgg acagagccca ttacaatatt     240 gtaaccttt gttgcaagtg tgactctacg cttcggttgt gcgtacaaag cacacacgta     300
gacattcgta ctttggaaga cctgttaatg ggcacactag gaattgtgtg ccccatctgt     360
tctcagaaac caggatcccg ggcacaccat caccatcacc attaa                     405

<210> SEQ ID NO 10
<211> LENGTH: 134
<212> TYPE: PRT
<213> ORGANISM: Artificial Sequence
<220> FEATURE:
<223> OTHER INFORMATION: Artificial Sequence Description: Protein fusion
      CPP LALF-E7
```

```
<400> SEQUENCE: 10

Met Ala Glu Phe His Tyr Arg Ile Lys Pro Thr Phe Arg Arg Leu Lys
 1               5                  10                  15

Trp Lys Tyr Lys Gly Lys Phe Trp Lys Ala Ser His Gly Asp Thr Pro
            20                  25                  30

Thr Leu His Glu Tyr Met Leu Asp Leu Gln Pro Glu Thr Thr Asp Leu
        35                  40                  45

Tyr Gly Tyr Glu Gln Leu Asn Asp Ser Ser Glu Glu Asp Glu Ile
 50                  55                  60

Asp Gly Pro Ala Gly Gln Ala Glu Pro Asp Arg Ala His Tyr Asn Ile
 65                  70                  75                  80

Val Thr Phe Cys Cys Lys Cys Asp Ser Thr Leu Arg Leu Cys Val Gln
                85                  90                  95

Ser Thr His Val Asp Ile Arg Thr Leu Glu Asp Leu Leu Met Gly Thr
            100                 105                 110

Leu Gly Ile Val Cys Pro Ile Cys Ser Gln Lys Pro Gly Ser Arg Ala
        115                 120                 125

His His His His His His
    130

<210> SEQ ID NO 11
<211> LENGTH: 30
<212> TYPE: DNA
<213> ORGANISM: Artificial Sequence
<220> FEATURE:
<223> OTHER INFORMATION: Artificial Sequence Description:Oligo primer
      PCR-GFP

<400> SEQUENCE: 11
ccaagcttca gtgagcaagg gcgaggagct                                    30

<210> SEQ ID NO 12
<211> LENGTH: 30
<212> TYPE: DNA
<213> ORGANISM: Artificial Sequence
<220> FEATURE:
<223> OTHER INFORMATION: Artificial Sequence Description:Oligo primer
      PCR-GFP

<400> SEQUENCE: 12 cgggatcccct tgtacagctc gtccatgccg                                   30

<210> SEQ ID NO 13
<211> LENGTH: 828
<212> TYPE: DNA
<213> ORGANISM: Artificial Sequence
<220> FEATURE:
<223> OTHER INFORMATION: Artificial Sequence Description: Gen fusion CPP
      LALF-GFP

<400> SEQUENCE: 13
atggcggaat tccattatcg tatcaaaccg acctttcgtc gtctgaaatg aaatataaa    60 ggcaaatttt ggaaagcttc agtgagcaag ggcgaggagc tgttcaccgg ggtggtgccc   120
atcctggtcg agctggacgg cgacgtaaac ggccacaagt tcagcgtgtc cggcgagggc   180
gagggcgatg ccacctacgg caagctgacc ctgaagttca tctgcaccac cggcaagctg   240
cccgtgccct ggcccaccct cgtgaccacc ctgacctacg gcgtgcagtg cttcagccgc   300
taccccgacc acatgaagca gcacgacttc ttcaagtccg ccatgcccga aggctacgtc   360
caggagcgca ccatcttctt caaggacgac ggcaactaca agacccgcgc cgaggtgaag   420
```

```
ttcgagggcg acaccctggt gaaccgcatc gagctgaagg gcatcgactt caaggaggac    480
ggcaacatcc tggggcacaa gctggagtac aactacaaca gccacaacgt ctatatcatg    540
gccgacaagc agaagaacgg catcaaggtg aacttcaaga tccgccacaa catcgaggac    600
ggcagcgtgc agctcgccga ccactaccag cagaacaccc ccatcggcga cggccccgtg    660
ctgctgcccg acaaccacta cctgagcacc cagtccgccc tgagcaaaga ccccaacgag    720
aagcgcgatc acatggtcct gctggagttc gtgaccgccg ccgggatcac tctcggcatg    780
gacgagctgt acaagggatc ccgggcacac catcaccatc accattaa                 828
```

<210> SEQ ID NO 14
<211> LENGTH: 275
<212> TYPE: PRT
<213> ORGANISM: Artificial Sequence
<220> FEATURE:
<223> OTHER INFORMATION: Artificial Sequence Description: Protein fusion
      CPP LALF-GFP <400> SEQUENCE: 14

```
Met Ala Glu Phe His Tyr Arg Ile Lys Pro Thr Phe Arg Arg Leu Lys
 1               5                  10                  15

Trp Lys Tyr Lys Gly Lys Phe Trp Lys Ala Ser Val Ser Lys Gly Glu
            20                  25                  30

Glu Leu Phe Thr Gly Val Val Pro Ile Leu Val Glu Leu Asp Gly Asp
        35                  40                  45

Val Asn Gly His Lys Phe Ser Val Ser Gly Glu Gly Glu Gly Asp Ala
    50                  55                  60

Thr Tyr Gly Lys Leu Thr Leu Lys Phe Ile Cys Thr Thr Gly Lys Leu
65                  70                  75                  80

Pro Val Pro Trp Pro Thr Leu Val Thr Thr Leu Thr Tyr Gly Val Gln
                85                  90                  95

Cys Phe Ser Arg Tyr Pro Asp His Met Lys Gln His Asp Phe Phe Lys
            100                 105                 110

Ser Ala Met Pro Glu Gly Tyr Val Gln Glu Arg Thr Ile Phe Phe Lys
        115                 120                 125

Asp Asp Gly Asn Tyr Lys Thr Arg Ala Glu Val Lys Phe Glu Gly Asp
    130                 135                 140

Thr Leu Val Asn Arg Ile Glu Leu Lys Gly Ile Asp Phe Lys Glu Asp
145                 150                 155                 160

Gly Asn Ile Leu Gly His Lys Leu Glu Tyr Asn Tyr Asn Ser His Asn
                165                 170                 175

Val Tyr Ile Met Ala Asp Lys Gln Lys Asn Gly Ile Lys Val Asn Phe
            180                 185                 190

Lys Ile Arg His Asn Ile Glu Asp Gly Ser Val Gln Leu Ala Asp His
        195                 200                 205

Tyr Gln Gln Asn Thr Pro Ile Gly Asp Gly Pro Val Leu Leu Pro Asp
    210                 215                 220

Asn His Tyr Leu Ser Thr Gln Ser Ala Leu Ser Lys Asp Pro Asn Glu
225                 230                 235                 240

Lys Arg Asp His Met Val Leu Leu Glu Phe Val Thr Ala Ala Gly Ile
                245                 250                 255

Thr Leu Gly Met Asp Glu Leu Tyr Lys Gly Ser Arg Ala His His His
            260                 265                 270

His His His
        275
```